(12) United States Patent
Vickery

(10) Patent No.: US 6,583,114 B2
(45) Date of Patent: Jun. 24, 2003

(54) FRACTURE HEALING USING PTHRP ANALOGS

(75) Inventor: Brian Henry Vickery, Los Altos Hills, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 09/146,802

(22) Filed: Sep. 3, 1998

(65) Prior Publication Data

US 2002/0077281 A1 Jun. 20, 2002

Related U.S. Application Data

(60) Provisional application No. 60/058,324, filed on Sep. 9, 1997.

(51) Int. Cl.[7] ........................ A61K 38/29; C07K 14/635
(52) U.S. Cl. ................................ 514/9; 514/11; 514/12; 530/307; 530/317; 530/324
(58) Field of Search .................................. 530/317, 324, 530/307; 514/9, 11, 12

(56) References Cited

U.S. PATENT DOCUMENTS 5,589,452 A    12/1996  Krstenansky et al. .......... 514/12
5,798,225 A  *  8/1998  Krstenansky et al. ...... 435/69.4

FOREIGN PATENT DOCUMENTS

| EP | 497915 | * | 8/1992 |
| JP | 08310965 | * | 11/1996 |
| WO | WO 94/01460 A1 | | 1/1994 |
| WO | WO 94/02510 A2 | | 2/1994 |
| WO | WO 95/02610 A1 | | 1/1995 |
| WO | WO 9502610 | * | 1/1995 |
| WO | WO 95/11697 A1 | | 5/1995 |
| WO | WO 96/40193 | | 12/1996 |
| WO | WO 96/40193 A | | 12/1996 |
| WO | WO 96/40775 A1 | | 12/1996 |
| WO | WO 97/02834 A1 | | 1/1997 |
| WO | WO 97/07815 | | 3/1997 |
| WO | WO 97/07815 A2 | | 3/1997 |
| WO | WO 98/30590 A2 | | 7/1998 |

OTHER PUBLICATIONS

Bilezikian, John P. et al, Eds., "Part I Basic Principles," Principles of Bone Biology, 412–413.

Hock, JM. et al., "Comparison of the Anabolic Effects of Synthetic Parathyroid Hormone–Related Protein (PTHrP) 1–34 and PTH 1–34 on bone in Rats," Endocrinology, vol. 125, 2022–2207, (1989).

Lanske, B. et al., "The Parathyroid Hormone (PTH)/PTH–Related Peptide Receptor Mediates Actions of Both Ligands in Murine Bone," Endocrinology, vol. 139., No. 12, 5194–5204 (1998).

Pilbeam, C.C. et al., "Comparison of the Effects of Various Lengths of Synthetic Human Parathyroid Hormone–Related Peptide (hPTHrP) of Malignancy on Bone Resoprtion and Formation in Organ Culture," Bone, vol. 14, 717–720 (1993).

Mierke, et al., "Conformational Studies of Mono–and Bicyclic Parathyroid Hormone–Related Protein–Derived Agonists," *Biochemistry*, (1997) pp 10372–10383, vol. 36.

Bisello, et al., *Biochemistry*, vol. 36, 1997, pp 3293–3299, "Mono–and Bicyclic Analogs of Parathyroid Hormone–Related Protein. 1. Synthesis and Biological Studies".

Fang, et al., *Proc. Natl. Acad. Sci. (U.S.A.)*, vol. 93, Jun. 1996, pp 5753–5758, "Stimulation of new bone formation by direct transfer of osteogenic plasmid genes".

Chorev, et al., *Biochemistry*, vol. 30, 1991, pp 5968–5974, "Cyclic Parathyroid Hormone Related Protein Antagonists: Lysine 13 to Aspartic Acid 17 [i+4)] Side Chain Lactamization".

Kim, et al., 43rd Annual Meeting, *Orthopaedic Research Soc.*, Feb. 9–13, 1997, San Francisco, California, vol. 22, Section 1, "Effect of Recombinant Human (1–84) Parathyroid Hormone on Fracture Healing in Ovariectomized Rats".

Kim, et al., *Journal of Bone and Mineral Research*, vol. 11:Supplement 1, Aug. 1996, Abstract No. P248, "Intermittent Treatment of PTH Improves Fracture Healing in Ovx. Rat".

* cited by examiner

Primary Examiner—Brenda Brumback
Assistant Examiner—Anish Gupta
(74) Attorney, Agent, or Firm—Rohan Peries

(57) ABSTRACT

This invention provides methods of bone healing and fracture repair comprising administering to a patient in need thereof an effective amount of a polypeptide analog of parathyroid hormone related peptide (PTHrP) and salts thereof, wherein amino acid residues 22–31 form an amphipathic α-helix. Systemic administration is a preferred mode of delivery.

28 Claims, 6 Drawing Sheets

Example of a high resolution radiograph of non-united defect at 6 weeks

Example of a high resolution radiograph of a healed defect at 6 weeks

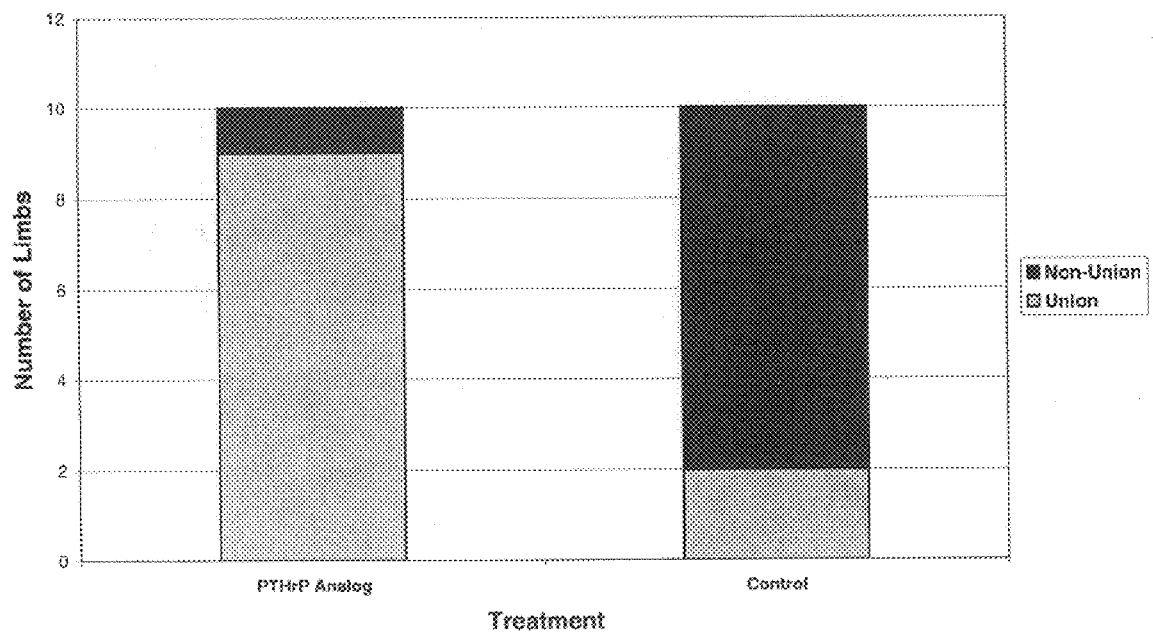
Figure 5  Union Rate at 6 Weeks

FRACTURE HEALING USING PTHRP ANALOGS

CROSS-REFERENCE TO RELATED APPLICATIONS

This application claims the benefit under 35 U.S.C. 119(e) of U.S. provisional patent application No. 60/058,324, filed Sep. 9, 1997.

```
Ala Val Ser Glu His Gln Leu Leu His Asp Lys Gly Lys Ser Ile
 1           5                  10                      15
    Gln Asp Leu Arg Arg Arg Phe Phe Leu His His Leu Ile Ala Glu
                 20                  25                      30
                    Ile His Thr Ala (SEQ ID NO:1).
```

BACKGROUND OF THE INVENTION

1. Field of the Invention

This invention relates to methods of bone healing and fracture repair.

2. Background Information

Approximately 8–10 million bone fractures are reported annually in the United States with more than 1 million of these requiring hospitalization. The estimated annual costs of treating these fractures exceeds 20 billion dollars. While this is already significant, these numbers are expected to increase due to the aging of the general population. Even though several therapies are indicated for preventing the bone loss associated with aging, there are fewer therapies indicated for treatment once a fracture has occurred. Most of these require local administration which is undesirable due to the complexity of delivery and poor patient compliance. Therefore, it would be desirable to have additional methods of facilitating bone healing and fracture repair.

It has recently been reported that intermittent treatment with parathyroid hormone (PTH) improves fracture healing in ovariectomized rats, indicating that PTH treatment may be potentially useful in treating postmenopausal osteoporotic fractures. "Effect of Recombinant Human (1–84) Parathyroid Hormone on Fracture Healing in Ovariectomized Rats," H. W. Kim et al.; *Transactions of the 43rd Annual Meeting of the Orthopaedic Research Society*, Vol. 22, Section 1, Abstract 181-31, Feb. 9–13, 1997, and "Intermittent Treatment of PTH Improves Fracture Healing in OVX Rat," H. W. Kim et al.; *Journal of Bone and Mineral Research*, Vol. 11, Supplement 1, page S152, Abstract P248 (August 1996). Other investigators have reported that implantation of a gene activated matrix expressing bone morphogenetic protein-4 and/or a fragment of PTH (amino acids 1–34) into the segmented defect rat fracture model causes formation of new bone which bridges the gap more rapidly than an untreated control. "Stimulation of New Bone Formation by Direct Transfer of Osteogenic Plasmid Genes," Jianming Fang et al.; *Proc. Natl. Acad. Sci. (USA)*, Vol. 93:5753–5758 (June 1996). Various PTH analogs have also been reported to be useful for treatment of osteoporosis (U.S. Pat. Nos. 5,556,940 and 5,559,792). Other methods of fracture healing include the use of is human platelet factor 4 (U.S. Pat. No. 5,622,935), benzothiophenes (U.S. Pat. No. 5,502,074) and 24,25(OH)$_2$ vitamin D$_3$ (U.S. Pat. No. 5,069,905).

PTH related peptide (PTHrP), previously known as the factor responsible for humoral hypercalcemia of malignancy, is a peptide of 138–174 amino acids (depending on alternative splicing) which binds to the PTH/PTHrP receptor. The N-terminal 34 amino acid sequence of PTHrP is of limited sequence homology to that of PTH, but in certain cases shows similar activity to PTH. However, PTHrP is generally less potent and less bone anabolic than PTH and has not been associated with fracture healing. The sequence of hPTHrP (1–34) is as follows:

Several truncated homologs and analogs of PTHrP have been reported. Analogs in which amino acid residues 22–31 of PTHrP(1–34) are replaced by an amphipathic α-helix (U.S. Pat. No. 5,589,452 and WO 97/07815) and related derivatives have been described as useful for treating osteoporosis. "RS-66271, A C-terminally Substituted Analog of Human Parathyroid Hormone-Related Protein (1–34) Increases Trabecular and Cortical Bone in Ovariectomized, Osteopenic Rats," B. H. Vickery et al. *J. Bone & Mineral Research*, 11(12):1943–1951 (1996) and "Modulation of Osteogenic Cell Ultrastructure by RS-23581, an Analog of Human Parathyroid Hormone (PTH)-Related Peptide-(1–34) and Bovine PTH-(1–34)," D. Leaffer et al. *Endocrinology*, 136(8):3624–3631 (1995). Monocyclic and bicyclic analogs of PTHrP (1–34) and PTHrP(7–34) were shown to bind strongly to the PTH receptor and stimulate (or antagonise) PTH-stimulated adenyl cyclase activity in osteoblast-like cells. "Mono- and Bicyclic Analogs of Parathyroid Hormone-Related Protein. 1. Synthesis and Biological Studies," Michael Chorev et al. *Biochemistry*, 36:3293–3299 (1997), and "Cyclic analogs of PTH and PTHrP," WO 96/40193.

SUMMARY OF THE INVENTION

In one aspect, this invention provides methods of bone healing and fracture repair comprising administering to a patient in need thereof an effective amount of a polypeptide analog of parathyroid hormone related peptide (PTHrP) and salts thereof, wherein amino acid residues 22–31 form an amphipathic α-helix composed of hydrophilic amino acids (Haa) and lipophilic amino acids (Laa) ordered in the sequence:

Haa(Laa Laa Haa Laa)$_2$Laa

When illustrative embodiments of this amphipathic helix are inserted into the PTHrP sequence, particularly into N-terminal truncates of human PTHrP (residues 1–32 through 1–38), the resulting polypeptides are effective in bone healing and fracture repair. Systemic administration is a preferred mode of delivery.

BRIEF DESCRIPTION OF THE DRAWINGS

FIG. 5 shows the union rate achieved in the corticosteroid induced delayed healing fracture model with PTHrP analog D, $(MAP_{1-10})^{22-31}hPTHrP(1-34)NH_2$.

DETAILED DESCRIPTION OF THE INVENTION

Nomenclature

Figure 1:
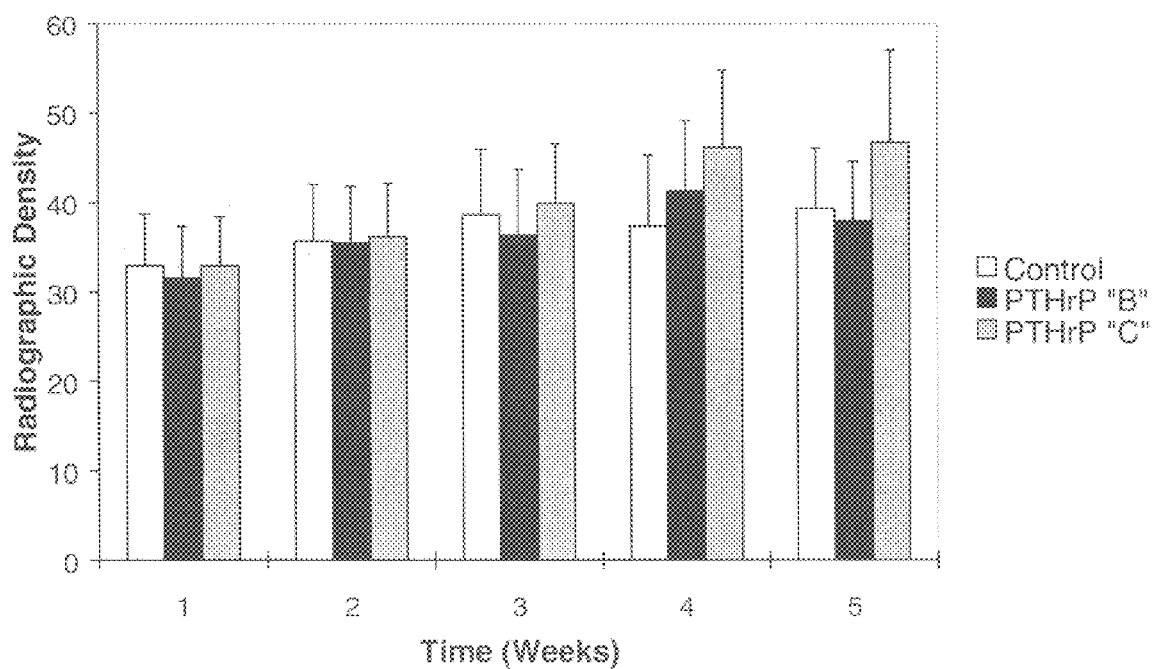
FIG. 1 shows the weekly radiographic density of a segmented bone defect in the rat fracture model over the course of five weeks of treatment with PTHrP analogs B or C relative to control. It shows that after four weeks, bone growth in the defects of animals treated with the PTHrP analogs was greater than in the control animals. PTHrP analogs B and C are (MAP$_{1-10}$)$^{22-31}$Ala$^{19}$hPTHrP(1–34)NH$_2$ and (MAP$_{1-10}$)$^{22-31}$His$^{26}$hPTHrP(1–34)NH$_2$ respectively.

The one- and three-letter abbreviations for the various common nucleotide bases and amino acids are as recommended in Pure Appl. Chem. 31: 639–645 (1972) and 40: 277–290 (1974) and comply with 37 CFR §1.822 (Jul. 1, 1996). The abbreviations represent L amino acids unless otherwise designated as D or D, L. Certain amino acids, both natural and non natural, are achiral, e.g. glycine. All peptide sequences are presented with the N terminal amino acid on the left and the C terminal amino acid on the right.

It will be recognized that both natural and unnatural amino acids may be present in the PTHrP analogs used in this invention. Examples of unnatural amino acids and their abbreviations include, homoserine (hSer), homoserine lactone (hSerlac), homocysteine (Hcy), homoarginine (hArg), homocitrulline (Hci), penicillamine (Pen), Nα-methylarginine (N-MeArg), norleucine (Nle), norvaline (Nval), norisoleucine (NIle), N-methylisoleucine (N-MeIle), phenylglycine (PhG), t-butylglycine (Tle), hydroxyproline (Hyp), 3,4-dehydroproline (Δ-Pro), pyroglutamine (Pyr, Glp), ornithine (Orn), 1-aminoisobutyric acid (1-Aib), 2-aminoisobutyric acid (2-Aib), 2-aminobutyric acid (2-Abu), 4-aminobutyric acid (4-Abu), 2,4-diaminobutyric acid (A2bu), α-aminosuberic acid (Asu), albizzin (Abz), β-cyclohexylalanine (Cha), 3-(1-naphthyl)alanine (1-Nal), 3-(2-naphthyl)alanine (2-Nal), citrulline (Cit). pipecolinic acid (Pip), 4-chlorophenylalanine (4-ClPhe), 4-fluorophenylalanine (4-FPhe), sarcosine (Sar) and 1-aminopropanecarboxylic acid (1-NCPC). Both natural and unnatural amino acids are commercially available from vendors such as NovaBiochem (San Diego, Calif.) and Bachem (Torrance, Calif.).

The PTHrP polypeptide analogs are described with reference to their variation from the native sequence of hPTHrP. The representation $(MAP_{1-10})$ refers to the particular amphipathic helical sequence shown below.

Glu Leu Glu Lys Leu Leu Glu Lys Leu (SEQ ID NO:2)

the MAP sequence of ten amino acid residues.

Thus, the sequence represented as $(MAP_{1-10})^{22-31}hPTHrP(1-34)$ refers to the 1–34 N-terminal residues of hPTHrP with the segment between residues 22–31 replaced by the MAP sequence. Within the MAP sequence, additional variants may be denoted. Thus, $(MAP_{1-10})^{22-31}His^{26}hPTHrP(1-34)$ refers to the 1–34 N-terminal residues of hPTHrP with the segment between residues 22–31 replaced by a MAP sequence in which there is a histidine at position 26 (instead of lysine as in the standard MAP sequence).

Additional variants from the naturally occurring sequence are similarly denoted. $(MAP_{1-10})^{22-31}Pro^{32}hPTHrP(1-32)$ refers to the 1–32 N-terminal residues of hPTHrP with the MAP sequence at positions 22–31 and a proline (replacing the naturally occurring histidine) at position 32. $(MAP_{1-10})^{22-31}D-Orn^{34}lactam$ hPTHrP (1–34) refers to the 1–34 N-terminal residues of hPTHrP with the MAP sequence at positions 22–31 and an ornithine at position 34 with a lactam formed between the amino group of the ornithine side chain and the carboxy terminus. $(MAP_{1-10})^{22-31}hSer^{34}hPTHrP(1-34)Thr$ His Ile Gln $NH_2$ refers to the 1–34 N-terminal residues of hPTHrP with the MAP sequence at positions 22–31, a homoserine at position 34, an additional sequence Thr His Ile Gln at positions 35–38 and the carboxy terminus being a primary amide.

Polypeptides with cyclized links between amino acid residues are denoted with the two linked residues placed within brackets and preceded by a "c." In general, the links between the two residues are formed between the side chain functionalities, typically as amide or ester bonds. Thus $(MAP\ 1-10)^{22-31}c[Lys^{13},\ Asp^{17}]hPTHrP(1-34)hSer^{34}$ lactone refers to the 1–34 N-terminal residues of hPTHrP with the segment between residues 22–31 replaced by the MAP sequence, the amino side chain of lysine at position 13 cyclized with the carboxyl side chain of aspartate at position 17 and an additional homoserine at position 34 with a lactone formed between the hydroxyl side chain of the homoserine and the carboxyl terminus. Similarly, $(MAP_{1-10})^{22-31}c[Lys^{13},\ Asp^{17}]hPTHrP(1-34)$ refers to the 1–34 N-terminal residues of hPTHrP with the segment between residues 22–31 replaced by the MAP sequence and the amino side chain of a lysine at position 13 cyclized with the carboxyl side chain of an aspartate at position 17.

"Hydrophilic amino acid (Haa)" refers to an amino acid having at least one hydrophilic functional group in addition to those required for peptide bond formation, such as arginine, asparagine, aspartic acid, glutamic acid, glutamine, histidine, lysine, serine, threonine, and their homologs.

"Lipophilic amino acid (Laa)" refers to an uncharged, aliphatic or aromatic amino acid, such as isoleucine, leucine, methionine, phenylalanine, tryptophan, tyrosine, valine, and their homologs.

For the purposes of this invention, alanine is classified as "amphiphilic" i.e., capable of acting as either hydrophilic or lipophilic.

A "polypeptide analog of PTHrP" refers to a polypeptide having art-accepted substitutions, deletions or insertions relative to PTHrP or is substantially homologous to PTHrP such that the analog has a similar physiological activity.

"Physiologically active truncated analog of PTHrP" refers to a polypeptide having a sequence comprising less than the full complement of amino acids found in PTHrP which, however, elicits a similar physiological response. The truncated PTHrP analogs need not be fully homologous with PTHrP to elicit a similar physiological response. Typically, the truncated analogs will be truncated from the C-terminus and will range from 30 to 40 residues, with PTHrP(1–32), PTHrP(1–34) and PTHrP(1–38) being preferred, but not exclusive, representatives of this group. Generally, the analogs will carry conservative substitutions of amino acids according to art-accepted parameters as described below.

The term "substantially homologous," when referring to polypeptides, indicates that the polypeptide in question exhibits at least about 80% homology, usually about 90% homology, and preferably 95% homology to the referenced polypeptide. Homology for polypeptides is typically measured using sequence analysis software. See, e.g., Sequence Analysis Software Package of the Genetics Computer Group, University of Wisconsin Biotechnology Center, 1710 University Avenue, Madison, Wis. 53705.

"Amphipathic a-helix" refers to the secondary structure exhibited by certain polypeptides in which the amino acids assume an a-helical configuration having opposing polar and nonpolar faces oriented along the long axis of the helix. Amphipathic helical sequences can be designed by those of skill in the art. Particular amphipathic helical sequences suitable for use in the methods of this invention are described in more detail in U.S. Pat. No. 5,589,452 and PCT Publication No. WO 97/07815.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)-benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Leaving group" has the meaning conventionally associated with it in synthetic organic chemistry i.e., an atom or group capable of being displaced by a nucleophile and includes halogen, alkanesulfonyloxy, arenesulfonyloxy, ester, or amino such as chloro, bromo, iodo, mesyloxy, tosyloxy, trifluorosulfonyloxy, methoxy, N,O-dimethylhydroxyl-amino, and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The present invention relates to the discovery that certain analogs of PTHrP containing an amphipathic α-helix at positions 22–31 are effective in bone healing and fracture repair. The amphipathic α-helix is composed of hydrophilic amino acids (Haa) and lipophilic amino acids (Laa) ordered in the sequence:

Haa (Laa Laa Haa Laa)$_2$ Laa When illustrative embodiments of this amphipathic helix are inserted into the PTHrP sequence, particularly into N-terminal truncates of human PTHrP (residues 1–32 through 1–38), the resulting polypeptides are effective in bone healing and fracture repair. Unlike PTH, PTHrP or analogs thereof not having this amphipathic helical segment, the analogs used herein do not cause hypercalcemia. In addition, these analogs induce a more rapid increase in bone relative to either PTH or PTHrP.

It will be recognized that in addition to containing an amphipathic helix between positions 22 and 31, a variety of substitutions, deletions and insertions of amino acids may be made in the PTHrP sequence outside this region while still preserving the three dimensional structure of the polypeptide. Representative variations of the PTH and PTHrP sequence which maintain the physiological activity of the resulting analogs are disclosed in U.S. Pat. Nos. 5,599,792, 5,556,940, 5,607,915 and 5,589,452, and PCT Publication Nos. WO91/06564, WO 94/02510, WO 95/11697, WO 96/40193 and WO 97/07815. Additional variants which will be expected by one of skill in the art to maintain physiological activity can be made by following art-accepted protein structure modeling techniques. Representative methodologies for deriving such variants are described inter alia in "Amino Acid Substitutions Preserve Protein Folding by Conserving Steric and Hydrophobicity Properties," I. Ladunga and R. F. Smith, *Protein Eng.*, 3:187–196 (1997) and "Constructing Amino Acid Residue Substitution Classes Maximally Indicative of Local Protein Structure," M. J. Thompson and R. A. Goldstein, *Proteins*, 1:28–37 (1996).

Substitutional variants are those in which at least one amino acid in the native sequence is removed and a different amino acid is put into its place at the same position. The substitutions may be single, where only one amino acid is replaced, or multiple where two or more amino acids are replaced in the same molecule. It is generally expected that any conservative substitutions will be permitted. Thus, an analog corresponding to substituting one hydrophilic amino acid for another hydrophilic amino acid or a hydrophobic amino acid for another hydrophobic amino acid is expected to maintain similar fracture healing properties to its precursor. Substitutions also include PTHrP analogs wherein the C-terminal residue is present as an amide. Additional substitutions may be made based on amino acids being either charged or uncharged. Each of these groups may be further divided into subgroups to further facilitate substitutions.

Charged Amino Acids

Acidic residues: aspartic acid, glutamic acid, 2-amino suberic acid

Basic residues: lysine, arginine, histidine, ornithine

Uncharged Amino Acids

Hydrophilic residues: serine, threonine, asparagine, glutamine, methionine

Aliphatic residues: glycine, alanine, valine, leucine, norleucine, isoleucine

Nonpolar residues: cysteine, homocysteine, methionine, proline

Aromatic residues: phenylalanine, tyrosine, tryptophan, histidine

Alternatively, amino acid substitutions may be based on the principal of bioisosterism. Such bioisosteric substitutions typically minimize any disruptive conformational effects that random substitution may create. The technique of alanine scanning may be used to identify positions where isosteric substitution is expected to provide variants which retain physiological activity. See "Structural and Mutational Analysis of Affinity-inert Contact Residues at the Growth Hormone-Receptor Interface," K. H. Pearce Jr., M. H. Ultsch, R. F. Kelley, A. M. de Vos and J. A. Wells, *Biochemistry*, 35 (32):10300–10307 (1996) and "Minimization of a Polypeptide Hormone," B. Li, J. Y. Tom, D Oare, R. Yen, W. J. Fairbrother, J. A. Wells and B. C. Cunningham, *Science*, 2701657–1660 (1995). Representative isosteric amino acids are shown in the table below.

| Amino acid | Isosteric amino acid |
|---|---|
| Ala | Ser, Gly |
| Glu | Gln, Asp |
| Gln | Asn, Glu |
| Asp | Asn, Glu |
| Asn | Ala, Asp |
| Leu | Met, Ile |
| Gly | Pro, Ala |
| Lys | Met, Arg |
| Ser | Thr, Ala |
| Val | Ile, Thr |
| Arg | Lys, Met, Asn |
| Thr | Ser, Val |
| Pro | Gly |
| Ile | Met, Leu, Val |
| Met | Ile, Leu |
| Phe | Tyr |
| Tyr | Phe |
| Cys | Ser, Ala |
| Trp | Phe, |
| His | Asn, Gln |

Deletional variants are those with one or more amino acids in the native amino acid sequence removed. Ordinarily, deletional variants will have one or two amino acids deleted in a particular region of the molecule. It is likely that deletions will be made at the ends of the sequence, particularly the carboxy terminus. Thus, though PTHrP (1–34) fragments are preferred, sequences which are further truncated at the carboxyl terminus also have bone healing effects.

Insertional or addition variants are those with the amino acid inserted immediately adjacent to an amino acid at a particular position in the native sequence. Immediately adjacent to an amino acid means connected to either the α-carboxy or α-amino group of the amino acid. Addition or insertion variants are also likely to be made at the ends of the sequence, again most likely at the carboxy terminus.

Of the above-listed modifications to the native sequence, substitutions, and carboxy terminus additions and deletions are preferred.

Preferred Embodiments

The polypeptide PTHrP analogs that are useful for fracture healing as described herein are generally described, in part, in U.S. Pat. No. 5,589,452 and PCT Publication No. WO 97/07815. Additional analogs include the cyclic analogs of N-terminal hPTHrP(1–32), hPTHrP(1–34) and hPTHrP (1–38) containing a MAP sequence between positions 22 and 31 and optionally having residues at positions 13 and 17 and/or 26 and 30 linked via their side chain functionalities. It will be recognized by one of skill in the art that a variety of substitutions can be made at postions 13 and 17 which would allow cyclization between those two positions.

PTHrP analogs of any mammalian species, e.g., human, bovine, porcine or rabbit may be used in this invention, with human PTHrP being preferred. One of skill in the art will recognize that substitution, deletion and insertion variants of the preferred embodiments enumerated below, according to the art-accepted principles described above, are also within the scope of the invention.

Preferred embodiments include the use of hPTHrP(1–34) analogs with a MAP sequence at positions 22–31, particularly those having a positively charged amino acid at position 26, e.g., lysine or histidine. Specific embodiments within this class are:

$(MAP_{1-10})^{22-31}hPTHrP(1-34)\ NH_2$

Ala Val Ser Gln His Gln Leu Leu His Asp Lys Gly Lys Ser Ile Gln Asp Leu Arg  (SEQ ID NO:3) and Arg Arg Glu Leu Leu Gln Lys Leu Leu Gln Lys Leu His Thr Ala $NH_2$ $(MAP_{1-10})^{22-31}His^{26}hPTHrP(1-34)\ NH_2$.

Ala Val Ser Gln His Gln Leu Leu His Asp Lys Gly Lys Ser Ile Gln Asp Leu Arg  (SEQ ID NO:4).

Arg Arg Gln Leu Leu Gln His Leu Leu Gln Lys Leu His Thr Ala $NH_2$

Other preferred embodiments include the use of hPTHrP (1–34) analogs with a MAP sequence at positions 22–31 and additionally containing a mono or bicyclic substructure created by cyclization between the side chain functionalities of the amino acid residues, particularly between residues 13 and 17 or between residues 26 and 30. The side chain functionalities are typically amino, hydroxy or carboxyl groups and cyclization occurs via the formation of an amide or ester bond. Residues with amino functionality on the side chain include lysine and ornithine. Residues with carboxyl functionality on the side chain include aspartic acid and glutamic acid. Specific embodiments within this class include:

(MAP$_{1-10}$)$^{22-31}$c[Lys$^{13}$,Asp$^{17}$]hPTHrP(1–34)hSer$^{34}$lactone

Ala Val Ser Glu His Gln Leu Leu His Asp Lys Gly Lys Ser Ile Gln Asp Leu Arg
Arg Arg Glu Leu Leu Glu Lys Leu Leu Glu Lys Leu His Thr hSerlac (SEQ ID NO:5) and (MAP$_{1-10}$)$^{22-31}$c[Lys$^{13}$,Asp$^{17}$]hPTHrP(1–34) NH$_2$.

Ala Val Ser Glu His Gln Leu Leu His Asp Lys Gly Lys Ser Ile Gln Asp Leu Arg
Arg Arg Glu Leu Leu Glu Lys Leu Leu Glu Lys Leu His Thr Ala NH$_2$ (SEQ ID NO:6).

Other hPTHrP analogs useful in this invention are the N-terminal sequences of between 30 to 50 residues, preferably from 1–32, 1–33, 1–34, 1–35, 1–36, 1–37 and 1–38, having the MAP sequence at residues 22–31 and optionally having a one or more substitutions at position 5, 13, 17, 19, 26, 30, 32 or 34. Specific embodiments within this class include: (MAP$_{1-10}$)$^{22-31}$Ile$^5$hPTHrP(1–34) NH$_2$

```
Ala Val Ser Glu Ile Gln Leu Leu His Asp Lys Gly Lys Ser Ile Gln Asp LeU Arg  (SEQ ID NO:7),

Arg Arg Glu Leu Leu Glu Lys Leu Leu Glu Lys Leu His Thr Ala NH2

(MAP1-10)22-31Ala19hPTHrP(1-34) NH2

Ala Val Ser Gln Ile Gln Leu Leu His Asp Lys Gly Lys Ser Ile Gln Asp Leu Ala  (SEQ ID NO:8),

Arg Arg Glu Leu Leu Glu Lys Leu Leu Gln Lys Leu His Thr Ala NH2

(MAP1-10)22-31Pro32hPTHrP(1-32) NH2

Ala Val Ser Glu Ile Gln Leu Leu His Asp Lys Gly Lys Ser Ile Gln Asp Leu Ala  (SEQ ID NO:9),

Arg Arg Gln Leu Leu Glu Lys Leu Leu Glu Lys Leu Pro NH2

(MAP1-10)22-31D-Orn34lactam hPTHrP (1-34)

Ala Val Ser Glu His Gln Leu Leu His Asp Lys Gly Lys Ser Ile Gln Asp Leu Arg  (SEQ ID NO:10),

Arg Arg Glu Leu Leu Glu Lys Leu Leu Glu Lys Leu His Thr D-Orn lactam (MAP1-10)22-31hPTHrP (1-34) A2bu34lactam Ala Val Ser Glu His Glu Leu Leu His Asp Lys Gly Lys Ser Ile Gln Asp Leu Arg  (SEQ ID NO:11) and Arg Arg Glu Leu Leu Gln Lys Leu Leu Gln Lys Leu His Thr A2bu lactam (MAP1-10)22-31hSer34PTHrP(1-34)THIQ NH2

Ala Val Ser Gln His Gln Leu Leu His Asp Lys Gly Lys Ser Ile Gln Asp Leu Arg  (SEQ ID NO 12).

Arg Arg Glu Leu Leu Glu Lys Leu Leu Glu Lys Leu His Thr hSer Thr His Ile

Gln NH2
```

Generally, all polypeptides substantially homologous to the specific embodiments disclosed herein are useful for the methods of the invention. Ordinarily, the polypeptides used in the present invention will be at least about 50%, preferably in excess of about 80%, and, more preferably in excess of about 90%, most preferably at least about 95% homologous to the specific embodiments disclosed herein. The length of polypeptide sequences compared for homology will be generally at least about 20 amino acids, usually at least about 24 residues, typically at least about 30 residues and preferably between 32 and 40 residues.

The compounds used in the present invention can be made by methods described in U.S. Pat. No. 5,589,452, and PCT Publications WO 96/40193 and WO 97/07815, all incorporated by reference herein. The compounds are generally made by solid phase synthesis, solution synthesis or recombinant methods which proceed via the cloning and expression of a gene coding for the polypeptide of interest, all known to one of skill in the art. Solid phase syntheses are preferred for truncated PTHrP analogs of forty or fewer amino acids. Analogs with cyclized side chains are generally prepared by assembling the complete protected polypeptide on the resin, removing the protecting groups and effecting the cyclization with an appropriate coupling agent, such as benzotriazol-1-yl-oxytris(pyrrolidino)phosphonium hexafluorophosphate (PyBOP) just before releasing the polypeptide from the resin.

Utility and Administration

The methods of treatment disclosed herein may be used for healing of bone fractures and osteotomies, including both union and nonunion fractures. Types of fractures treatable by the methods of this invention include both traumatic and osteoporotic fractures, e.g., fractures of the hip, neck of the femur, wrist, vertebrae, spine, ribs, sternum, larynx and trachea, radius/ulna, tibia, patella, clavicle, pelvis, humerus, lower leg, fingers and toes, face and ankle. Other uses include facilitating joint fusions, e.g., fusions of the spine, ankle and foot, elbow, hip and arthredoses of the hip, knee and shoulder. Treatment with the PTHrP analogs as described herein is also indicated in conjunction with arthroplastic procedures (including revision arthroplasties) of the hip, knee, shoulder/elbow etc. Bone healing may also be enhanced in other surgical settings such as in cranio and maxillofacial surgery, dental surgery and bunionectomy. PTHrP analogs have been shown to accelerate healing both in endochrondral bone (Examples 1 and 2) which proceeds via cartilagenous callous formation, as well as in intramembraneous bone (Example 3) which does not require intermediate callous formation. Healing in intramembraneous bone is particularly useful in cases where fracture healing is delayed, e.g., in diabetics, smokers, geriatrics, anemic patients, and patients undergoing corticosteroid (particularly chronic glucocorticoids), chronic NSAID or immunosuppressive therapy.

The particular dosage of a PTHrP analog required to facilitate fracture healing according to this invention will depend on the severity of the condition, the route of administration and related factors which will be decided by the attendant physician. Typically, the dosage will range between about 0.01 and 10 µg/kg body weight per day, preferably from about 0.1 to about 0.5 fg/kg body weight per day. For a 50 kg human subject, the daily dose of active ingredient is from about 0.5 to about 100 µgs, preferably from about 5 to about 10 µgs. This dosage may be delivered in a conventional pharmaceutical composition by a single administration, by multiple applications, or via controlled release, as needed to achieve the most effective results. Dosing will continue for as long as is medically indicated, which depending on the severity of the injury may range from a few weeks to several months.

Unlike most currently available methods of treating fractures, the PTHrP analogs can be administered systemically. Representative delivery regimens include oral, parenteral (including subcutaneous, intramuscular and intravenous), rectal, buccal (including sublingual), transdermal, pulmonary and intranasal. Typical pulmonary and respiratory delivery systems are described in U.S. Pat. No. 5,607,915. Nasal delivery of PTHrP analogs is described in PCT Publication No. WO 97/07815. Also included in the treatment methods of this invention are systemic administration of PTHrP analogs in conjunction with local treatment of a second bone healing agent. Representative agents for such local administration include the bone morphogenetic proteins (BMP-2 and BMP-7), osteogenic proteins (OP-1), growth factors such as TGF-β1 and cytokines such as IFN-β. Typically these agents are delivered locally in various carriers such as hydroxyapatite and/or calcium carbonate and amylopectin. Systemic administration of PTHrP analogs may also be combined with alternative methods of fracture healing such as mechanical or biophysical stimulation, e.g., electrical or ultrasound.

PTHrP analogs will typically be administered as pharmaceutical compositions in admixture with a pharmaceutically acceptable, non toxic carrier. As mentioned above, such compositions may be prepared for parenteral (subcutaneous, intramuscular or intravenous) administration, particularly in the form of liquid solutions or suspensions; for oral or buccal administration, particularly in the form of tablets or capsules; for intranasal administration, particularly in the form of powders, nasal drops or aerosols; and for rectal or transdermal administration.

Liquid formulations for parenteral administration may contain as excipients sterile water or saline, alkylene glycols such as propylene glycol, polyalkylene glycols such as polyethylene glycol, oils of vegetable origin, hydrogenated naphthalenes and the like. They may employ slightly acidic buffers in pH ranges of about 4 to about 6. Suitable buffers include acetate, ascorbate and citrate at concentrations ranging from about 5 mM to about 50 mM. For oral administration, the formulation can be enhanced by the addition of bile salts or acylcamitines. Formulations for nasal administration may be solid and may contain excipients, for example, lactose or dextran, or may be aqueous or oily solutions for use in the form of nasal drops or metered spray. Particular nasal formulations include dry powders suitable for conventional dry powder inhalers (DPI's), liquid solutions or suspensions suitable for nebulization and propellant formulations suitable for use in metered dose inhalers (MDI's). For buccal administration typical excipients include sugars, calcium stearate, magnesium stearate, pregelatinated starch, and the like.

When formulated for nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

The following are representative pharmaceutical formulations for using PTHrP analogs as described herein for bone healing and fracture repair.

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
|---|---|
| compound of this invention | 0.2 g |
| sodium acetate buffer solution, 0.4M | 2.0 ml |
| HCl (1N) or NaOH (1N) | q.s. to suitable pH |
| water (distilled, sterile) | q.s. to 20 ml |

Nasal Formulation

The following ingredients are mixed to form a suspension for nasal administration.

| Ingredient | Amount |
|---|---|
| PTHrP analog | 20 mg/ml |
| citric acid | 0.2 mg/ml |
| sodium citrate | 2.6 mg/ml |
| benzalkonium chloride | 0.2 mg/ml |
| sorbitol | 35 mg/ml |
| sodium taurocholate or glycocholate | 10 mg/ml |

The following preparations and examples are given to enable those skilled in the art to more clearly understand and to practice the present invention. They should not be considered as limiting the scope of the invention, but merely as being illustrative and representative thereof.

EXAMPLE 1

Healing of Segmented Fracture Defects with PTHrP Analogs

A modification of the segmental femoral defect rat model was used to demonstrate that PTHrP analogs facilitate bone healing and fracture repair. T. A. Einhorn et al. "The Healing of Segmented Bone Defects Induced by Demineralized Bone Matrix. A Radiographic and Biomechanical Study," J. Bone Joint, 66:274–279 (1984.

Adult male Sprague-Dawley rats weighing about 300 grams were maintained on Laboratory Rodent Diet 5001 (PMI Feeds, St. Louis, Mo.) and water ad libitum. All rats received only water for 12 hours prior to surgery. The animals were anesthetized prior to surgery by IP injection with ketamine (80 mg/kg) and xylazine (5 mg/kg). A single dose of procaine penicillin was given intramuscularly for prophylaxis against infection.

A lateral approach to the femur was used and a pre-drilled high density polyethylene plate was fixed along the anterior cortex of the femur. During this placement the periosteum of the femur was extensively stripped. A 1 mM non-critical sized segmental defect was created in the mid portion of the femur shaft. The wound was closed with nylon and chromic sutures.

Postoperatively, the rats were placed in cages with 48 hour post-operative access to food pellets. The animals were monitored at least once daily and animals displaying any signs of illness were examined and given appropriate therapy if necessary.

Rats were divided into groups as shown in Table 1 and either a control vehicle (saline) or a PTHrP analog as described herein was administered subcutaneously daily starting on post-operative day 1. Radiographic analyses were performed weekly. Animals were sacrificed at 6 weeks and compared by radiography.

Figure 2:
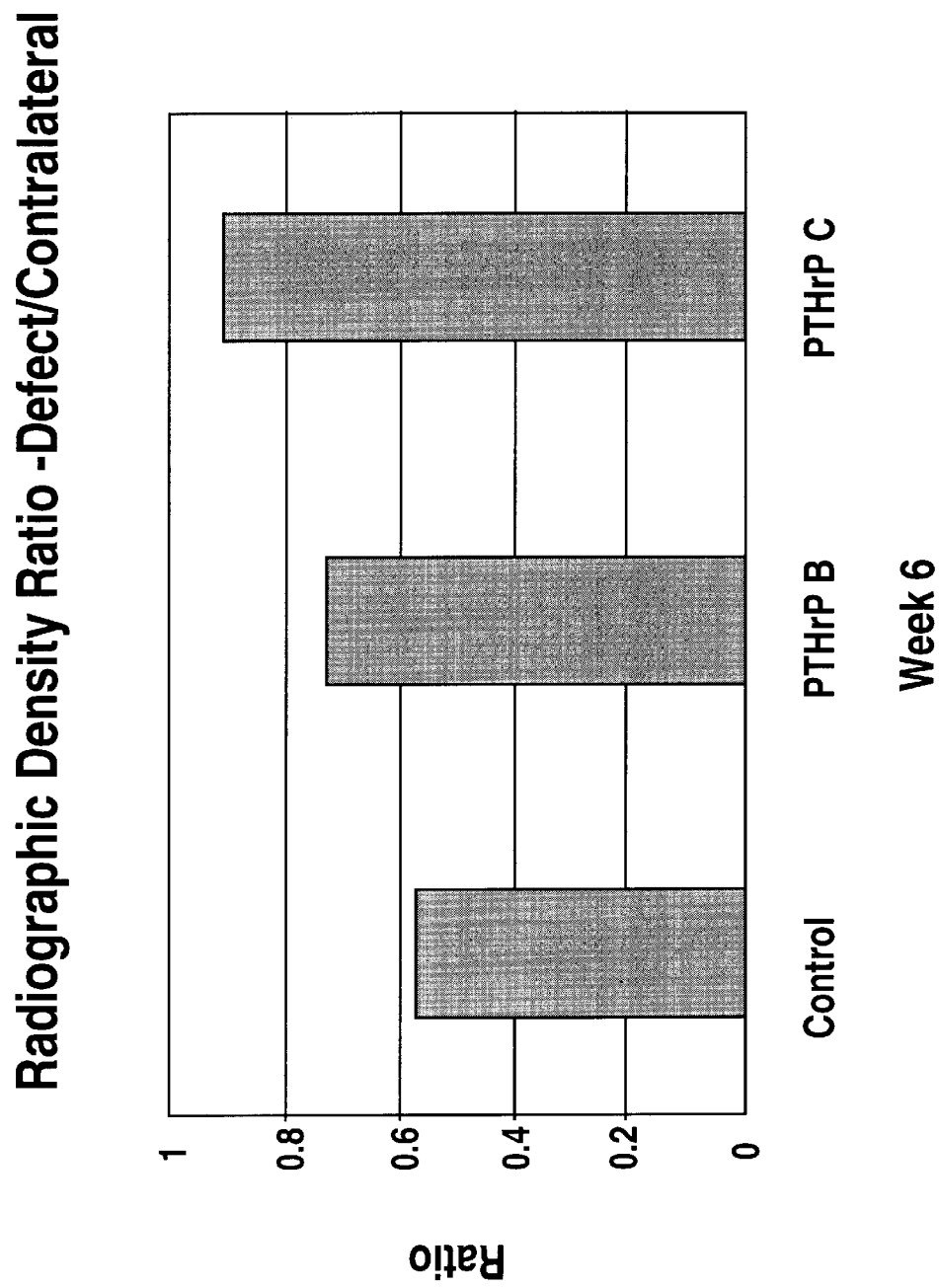
FIG. 2 shows the radiographic density ratio of the segmented bone to the contralateral femur (control) in the segmented defect rat fracture model after six weeks of treatment with control or PTHrP analogs B or C. Rats treated with PTHrP analogs B and C had an increased bone density relative to control treated rats.

Sedated rats were placed in the prone position with hindlimbs externally rotated. Serial radiographs of each femur (involved femur and contralateral femur) were taken weekly starting with postoperative week 1. An aluminium phantom device with known density values was included in each radiograph for calibration. Each radiograph was placed on a translumination board and a picture taken using a DCS 420 digital Kodak camera. These images were then transferred to a Gateway 2000 IBM compatible computer and digitized using image analysis software (Sigma Scan©). An outline of the defect was traced and the average density of the area of the osteotomy measured in treated animals relative to control animals. FIG. 1 shows the increase in bone density of the osteotomy in treated animals relative to control animals at weekly intervals over the first five weeks of treatment. The average density of the osteotomy was also compared to the average density of the contralateral femur for each weekly reading. FIG. 2 shows the radiographic density ratio after six weeks. Comparison of these bone densities showed that the PTHrP analogs had a bone healing effect. After sacrifice (6 weeks), the femurs (experimental and contralateral) were dissected free of soft tissue. Fine grain radiographs were taken of the femurs in the lateral plane. The osteotomy was considered united when there was osseous continuity of the femur across more than 25% of the cross sectional diameter of the defect. Comparison of femurs from treated animals to control animals showed that PTHrP analogs accelerated bone healing and fracture repair.

Figure 3A:
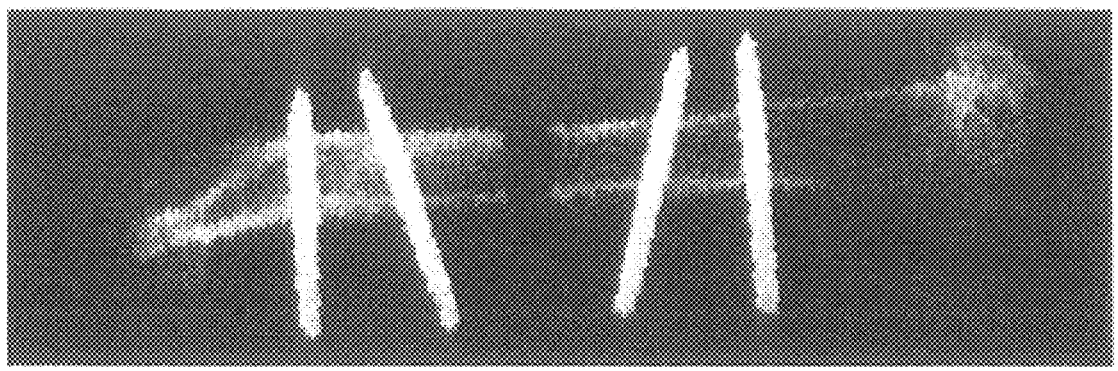
FIG. 3 shows high resolution radiographs of bone defects in the segmented defect rat fracture model of rats after treatment for six weeks with either control (3A) or PTHrP analog C (3B). The radiograph demonstrates that the control defect remains non-united whereas the defect treated with PTHrP analog C has healed.
Figure 3B:
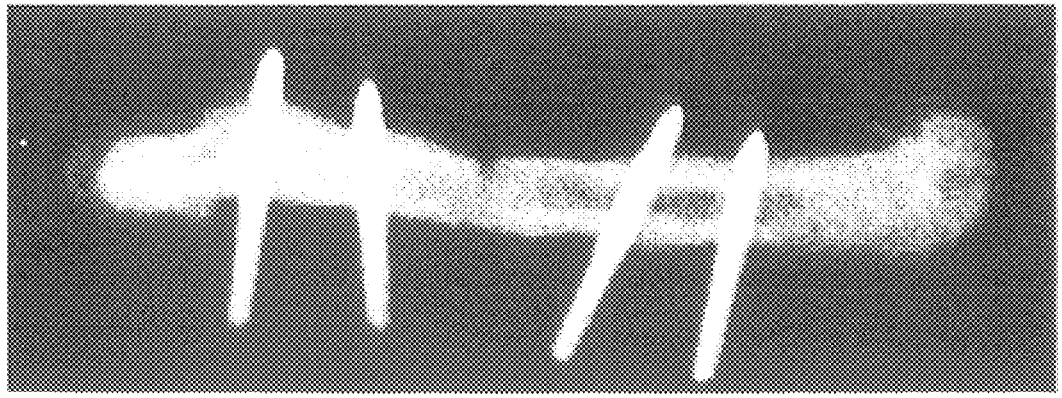

The first experiment tested PTHrP analogs B and C and FIG. 3 shows a representative radiograph from control (FIG. 1A) and treated (FIG. 1B) animals.

TABLE 1

| Group | Compound | Administration | # of Animals | Sacrifice |
|---|---|---|---|---|
| 1 | Control | subcutaneous | 10 | six weeks |
| 2 | PTHrP analog B | subcutaneous | 10 | six weeks |
| 3 | PTHrP analog C | subcutaneous | 10 | six weeks |

A second experiment tested the additional PTHrP analogs $(MAP_{1-10})^{22-31}c[Lys^{13}, Asp^{17}]hPTHrP(1-34)NH_2$ and $(MAP_{1-10})^{22-31}hSer^{34}PTHrP(1-34)THIQ\ NH_2$ and these analogs also accelerated bone healing and fracture repair.

EXAMPLE 2
Bone Healing in the Closed Fracture Defect Model with PTHrP Analogs The closed fracture model used is the Bonnarens/Einhorn model. F. Bonnarens and T. A. Einhorn, "Production of a Standard Closed Fracture in Laboratory Animal Bone," *J. Orthopaedic Research*, 2:97–101(1984). The rats used are as in Example 1. In this model an intramedullary rod is placed retrograde through the distal femur via a medial parapatellar approach. The arthrotomy is then closed with non-resorbable sutures and the intramedullary rod is left in place. A closed transverse fracture is then created by a custom made three point clamping device. The animals are monitored and radiographic analysis is performed as in Example 1. PTHrP analogs accelerated bone healing and fracture repair in this model in treated animals relative to control animals.

EXAMPLE 3
Intramembraneous Bone Healing with PTHrP Analogs

Rabbits were generally anesthesized and subjected to surgery to create four surface defects, one in each distal femur and one in each proximal tibia. A posterior lateral surgical incision measuring approximately 3 cm. was made to expose the distal lateral femoral condyle. Bone proximal to the knee joint was subperiosteally exposed and a 5 mm drill hole was made, keeping the drill bit cool by constant irrigation. The wound was irrigated with normal saline. Deep tissue was closed with a running 3-0 chronic suture followed by closure of the subticular layer with a running 3-0 nylon suture and three to four interrupted stainless steel sutures. A second 3 cm. incision was made over the medial proximal tibia and a 5 mm drill hole was made in the proximal medial tibia. The wound was closed as described previously. The entire procedure was repeated on the contralateral limb.

Stock solutions of PTHrP analog C, $(MAP_{1-10})^{22-31}His^{26}hPTHrP(1-34)NH_2$, and PTHRP analog D, $(MAP_{1-10})^{22-31}hPTHrP(1-34)NH_2$, at 800 µg/ml were prepared by sterile filtration through an 0.22 micron filter and diluted in vehicle to either 20 µg/ml or 100 µg/ml just before administration. Vehicle was 30 mg/ml mannitol, 30/mg/ml sucrose, 0.12 mg/ml Tween™ 80, 0.17 mg/ml acetic acid and 2.33 mg/ml sodium acetate trihydrate. PTHrP analogs at either 2 µg/kg/day or 10 µg/kg/day was administered daily by subcutaneous injection to the surgically treated animals.

Animals were X-rayed weekly for the duration of the study. Densitometric measurements were made using a transilluminating scanner and MetaMorph™ (Universal Imaging, West Chester, Pa.) software. Radiographs of the lower extremities were performed in internal and external rotation on post-operative day 10 and 21. The animals were sacrificed on post-operative day 30. At the end of the study, animals were euthanized by pentobarbital overdose, tissues were harvested from the left and right femurs and tibias were analyzed by x-ray and histological analysis.

Figure 4A:
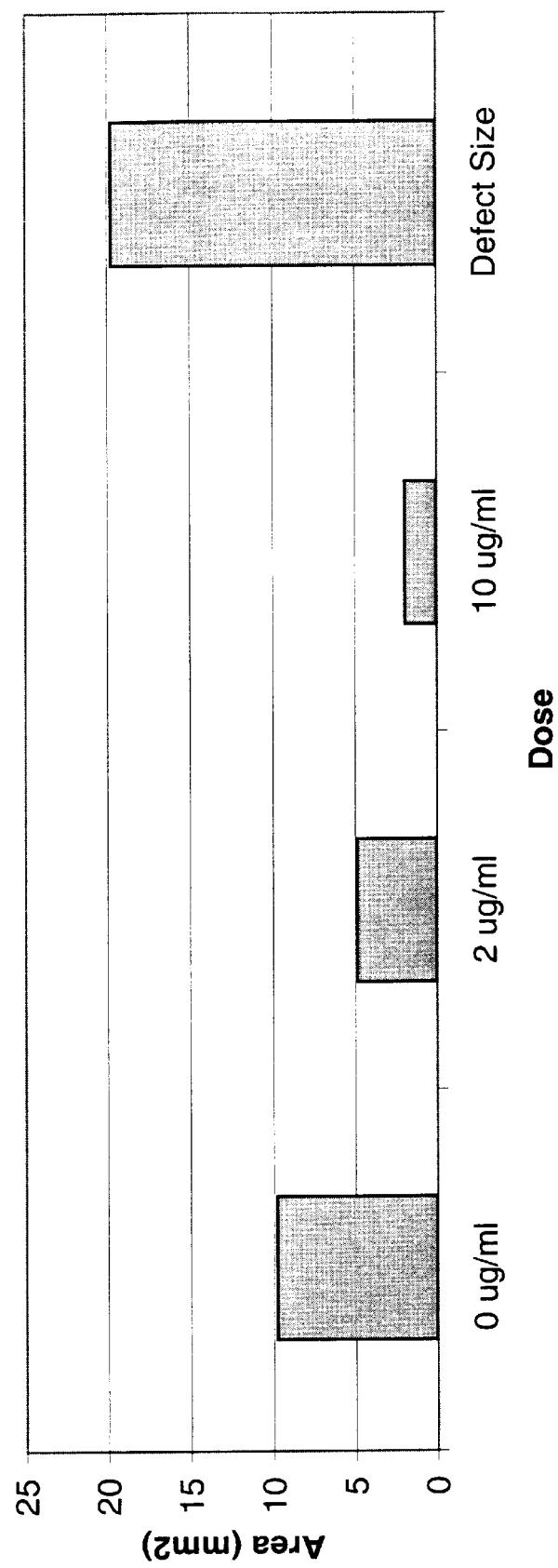
FIGS. 4A and 4B show the healing of an intramembraneous bone defect in rabbits after treatment with PTHrP analog D, $(MAP_{1-10})^{22-31}hPTHrP(1-34)NH_2$ at two different doses.
Figure 4B:
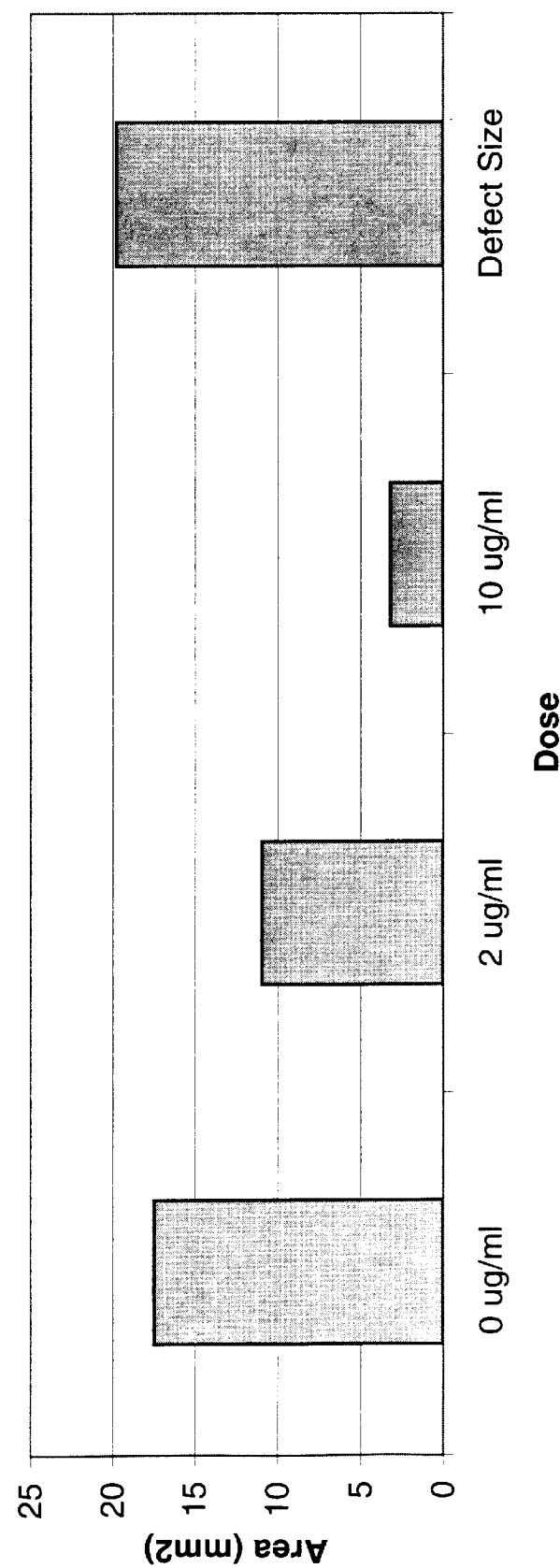

The animals treated with PTHrP analogs C and D showed accelerated intramembraneous bone formation relative to vehicle treated animals. The results for PTHrP analog D are shown in FIGS. 4A and 4B for the femur and tibia respectively. By day 21 there was no complete healing in either of the femoral or tibial defects in the control treated animals whereas 40% of the of the femoral and tibial defects had healed in the low dose group had healed. At this same time point, 75% of the tibial defects and 50% of the femoral defects had healed in the high dose group. At sacrifice, radiographic analysis of the specimens confirmed the enhancement of healing in the PTHrP analogue treated animals with over 85% of the high dose tibial defects filled with mineralized tissue while less than 10% of the control tibial defects were filled at sacrifice (p<0.01). Similarly, there was a significant greater percent fill in the PTHrP treated femoral defects than the control treated femoral defects (p<0.01).

EXAMPLE 4
Enhanced Bone Healing in the Ulnar Osteotomy Model

The purpose of this experiment was to demonstrate that PTHrP analogs can increase the biomechanical strength (Part I) and the kinetics of healing (Part II) in the context of systemic corticosteroid therapy in a rabbit osteotomy model.

Adult male New Zealand White rabbits were used in all experiments. In Part I, ten rabbits were divided into two equal groups and in Part II, twenty rabbits were divided equally. Non critical sized (1 mm) defects were created bilaterally in each rabbit. From two months prior to surgery through six weeks post-operative, all rabbits received daily subcutaneous injections of either prednisone (0.15 mg/kg) in sterile water (experimental group) or sterile saline (control group). Beginning on the first post-operative day, the experimental group were administered daily sub cutaneious infections of PTHrP analog D (0.01 mg/kg), while the control group received injections of normal saline. In Part I, animals were sacrificed at six weeks after creation of the osteotomy. In Part II, animals were sacrificed once radiographic union was reached bilaterally, or in cases of non-union at ten weeks post-operative.

In both sets of experiments, radiological intensity and healing area were analyzed every other week starting two weeks (Part I) or four weeks (Part II) post-operatively. Serial radiographs of the forelimbs were taken and digitized and the bone area was quantified using image analysis software (Sigma Scan Pro). Photodensitometry was used to quantitate the mineral content of the newly formed bone at sites of osteotomy and callus formation. After sacrifice, high resolution faxitron radiographs were taken of both limbs in the anteroposterior and lateral planes, allowing for analysis of fracture callus dimension and size.

Results—(Part I)

Nine out ten PTHrP analog D treated limbs achieved union in six weeks, while only two out of ten achieved union in the vehicle treated controls. These results are shown in FIG. 5. At six weeks both anteroposterior and lateral faxitrons revealed significantly greater intensities at the osteotomy sites of treated versus control limbs. Similarly, the intensity of both the proximal and distal ulnar diaphyses was significantly greater in the treated limbs. Laterally, the intensity of the external calluses was also greater in the treated limbs. Biomechanically, the torsional strength of the treated limbs was significantly greater than the vehicle-treated control limbs in terms of both stiffness and maximum torque.

Results—(Part II)

At four weeks, the treated limbs demonstrated greater radiographic intensity than the control limbs at the osteotomy site (p<0.01) as well as in the external calluses and ulnar diaphyses. The combined callus areas of the treated limbs was greater (p<0.05) and there was a trend indicating that the osteotomy site was decreasing in size. At six weeks, in vivo radiography demonstrated a trend of increased intensity at the osteotomy site of the treated limbs compared to the control limbs, although no differences were observed in callus intensity or area. Radiographically, all the PTHrP analog treated limbs were treated as united and all these animals were sacrificed at six weeks. At eight weeks, four additional limbs (two animals) reached radiographic union and were sacrificed. At ten weeks, the remaining animals were sacrificed, since these limbs showed no radiographic progression towards healing over the preceding four-week period and were thus classified as non-unions. The PTHrP analog treated limbs showed a greater radiographic intensity at the osteotomy site (p<0.05), as well as the ulnar diaphysis and the callus area. The area of the osteotomy was significantly smaller in the PTHrP analog treated limbs than in the vehicle control limbs. Thus in this corticosteroid induced model of delayed healing, PTHrP analog treatment resulted in a complete union rate at six weeks while 75% of untreated limbs showed no tendency to unite at ten weeks.

The foregoing invention has been described in some detail by way of illustration and example, for the purposes of clarity and understanding. It will be obvious to one of ordinary skill in the art that changes and modifications may be practiced within the scope of the appended claims. Therefore, it is to be understood that the above description is intended to be illustrative and not restrictive. The scope of the invention should, therefore, be determined with reference to the following appended claims, along with the full scope of equivalents to which such claims are entitled.

The patents, patent applications and publications cited in this application are hereby incorporated by reference in their entirety for all purposes to the same extent as if each individual patent, patent application or publication were so individually denoted.

What is claimed is:

1. A method of bone fracture repair comprising administering to a patient in need thereof a therapeutically effective amount of a polypeptide analog of parathyroid hormone related peptide (PTHrP) and salts thereof, in which amino acid residues 22–31 of said PTHrP analog form an amphipathic I-helix, for a time and under conditions to achieve said fracture repair.

2. The method of claim 1, wherein the amphipathic I-helix is Glu Leu Leu Glu Xaa Leu Leu Glu Lys Leu (5Xaa-SEQ ID NO:2) wherein Xaa is a positively charged amino acid residue.

3. The method of claim 2, wherein Xaa is lysine or histidine.

4. The method of claim 3, wherein the PTHrP analog is:

```
Ala Val Ser Glu His Gln Leu Leu His Asp Lys Gly Lys Ser Ile Gln Asp Leu Arg

Arg Arg Glu Leu Leu Glu Lys Leu Leu Glu Lys Leu His Thr Ala NH₂           (SEQ ID NO:3) or

Ala Val Ser Glu His Gln Leu Leu His Asp Lys Gly Lys Ser Ile Gln Asp Leu Arg

Arg Arg Glu Leu Leu Glu His Leu Leu Glu Lys Leu His Thr Ala NH₂           (SEQ ID NO:4).
```

5. The method of claim 2, wherein the PTHrP analog has at least two amino acid residues linked via their side chains to each other.

6. The method of claim 5, wherein the linked amino acid residues are at positions 13 and 17 or at positions 26 and 30.

7. The method of claim 6, wherein the amino acid residue at position 17 is an aspartic acid.

8. The method of claim 7, wherein the PTHrP analogs are:

Ala Val Ser Glu His Gln Leu Leu His Asp Lys Gly L⌐ys Ser Ile Gln A⌐sp Leu Arg   (SEQ ID NO:5) or
Arg Arg Glu Leu Leu Glu Lys Leu Leu Glu Lys Leu His Thr hSerlac Ala Val Ser Glu His Gln Leu Leu His Asp Lys Gly L⌐ys Ser Ile Gln A⌐sp Leu Arg   (SEQ ID NO:6).
Arg Arg Glu Leu Leu Glu Lys Leu Leu Glu Lys Leu His Thr Ala NH₂

9. The method of claim 1, wherein the PTHrP analog comprises an N-terminal truncation of 30 to 50 amino acid residues with at least one residue optionally substituted at any one of positions 5, 13, 17, 19, 26, 30, 32 and/or 34.

10. The method of claim 9, wherein the PTHrP analog is:

```
Ala Val Ser Glu Ile Gln Leu Leu His Asp Lys Gly Lys Ser Ile Gln Asp Leu Arg   (SEQ ID NO:7),

Arg Arg Glu Leu Leu Glu Lys Leu Leu Glu Lys Leu His Thr Ala NH₂
```

-continued

```
Ala Val Ser Glu Ile Gln Leu Leu His Asp Lys Gly Lys Ser Ile Gln Asp Leu Ala   (SEQ ID NO:8),

Arg Arg Glu Leu Leu Gln Lys Leu Leu Glu Lys Leu His Thr Ala NH2

Ala Val Ser Gln Ile Gln Leu Leu His Asp Lys Gly Lys Ser Ile Gln Asp Leu Ala   (SEQ ID NO:9),

Arg Arg Glu Leu Leu Gln Lys Leu Leu Glu Lys Leu Pro NH2

Ala Val Ser Glu His Gln Leu Leu His Asp Lys Gly Lys Ser Ile Gln Asp Leu Arg   (SEQ ID NO:10),

Arg Arg Glu Leu Leu Gln Lys Leu Leu Glu Lys Leu His Thr D-Orn lactam

Ala Val Ser Glu His Gln Leu Leu His Asp Lys Gly Lys Ser Ile Gln Asp Leu Arg   (SEQ ID NO:11) or

Arg Arg Glu Leu Leu Glu Lys Leu Leu Glu Lys Leu His Thr hSer lactam

Ala Val Ser Glu His Gln Leu Leu His Asp Lys Gly Lys Ser Ile Glu Asp Leu Arg   (SEQ ID NO 12).

Arg Arg Glu Leu Leu Glu Lys Leu Leu Glu Lys Leu His Thr HSer Thr His Ile

Gln NH2
```

11. The method of claim 1, wherein the PTHrP analog is administered systemically.

12. The method of claim 11, wherein the PTHrP analog is administered by nasal delivery.

13. The method of claim 1, further comprising locally administering a second bone healing agent to the fracture.

14. The method of claim 1 wherein the fracture is in intramembraneous bone.

15. A method of treatment for non-union bone fracture repair comprising administering to a patient in need thereof a therapeutically effective amount of a polypeptide analog of PTHrP and salts thereof, in which amino acid residues 22-31 of said PTHrP analog form an amphipathic I-helix, for a time and under conditions to achieve said fracture repair.

16. The method of claim 15, wherein the amphipathic α-helix is

Glu Leu Leu Glu Xaa Leu Leu Glu Lys Leu ($^5$Xaa-SEQ ID NO:2)

wherein Xaa is a positively charged amino acid residue.

17. The method of claim 16, wherein Xaa is lysine or histidine.

18. The method of claim 17, wherein the PTHrP analog is:

```
Ala Val Ser Glu His Gln Leu Leu His Asp Lys Gly Lys Ser IleGln Asp Leu Arg    (SEQ ID NO:3) or

Arg Arg Glu Leu Leu Glu Lys Leu Leu Glu Lys Leu His Thr Ala NH2

Ala Val Ser Glu His Gln Leu Leu His Asp Lys Gly Lys Ser IleGln Asp Leu Arg    (SEQ ID NO:4).

Arg Arg Glu Leu Leu Glu His Leu Leu Glu Lys Leu His Thr Ala NH2
```

19. The method of claim 16, wherein the PTHrP analog has at least two amino acid residues linked via their side chains to each other.

20. The method of claim 19, wherein the linked amino acid residues are at positions 13 and 17 or at positions 26 and 30.

21. The method of claim 20, wherein the amino acid residue at position 17 is an aspartic acid.

22. The method of claim 21, wherein the PTHrP analogs are:

(SEQ ID NO:5)
```
Ala Val Ser Glu His Gln Leu Leu His Asp Lys Gly Lys Ser Ile Gln Asp Leu  Arg Arg Arg
Glu Leu Leu Glu Lys Leu Leu Glu Lys Leu His Thr hSerlac
```
or (SEQ ID NO:6)
```
Ala Val Ser Glu His Gln Leu Leu His Asp Lys Gly Lys Ser Ile Gln Asp Leu  Arg Arg Arg
Glu Leu Leu Glu Lys Leu Leu Glu Lys Leu His Thr Ala NH2.
```

23. The method of claim 15, wherein the PTHrP analog comprises an N-terminal truncation of 30 to 50 amino acid residues with at least one residue optionally substituted at any one of positions 5, 13, 17, 19, 26, 30, 32 and/or 34.

24. The method of claim 23, wherein the PTHrP analog is:

```
Ala Val Ser Glu Ile Gln Leu Leu His Asp Lys Gly Lys Ser Ile Gln Asp Leu Arg  (SEQ ID NO:7);

Arg Arg Glu Leu Leu Glu Lys Leu Leu Glu Lys Leu His Thr Ala NH2

Ala Val Ser Glu Ile Gln Leu Leu His Asp Lys Gly Lys Ser Ile Gln Asp Leu Ala  (SEQ ID NO:8);

Arg Arg Glu Leu Leu Glu Lys Leu Leu Glu Lys Leu His Thr Ala NH2

Ala Val Ser Glu Ile Gln Leu Leu His Asp Lys Gly Lys Ser Ile Gln Asp Leu Ala  (SEQ ID NO:9);

Arg Arg Glu Leu Leu Glu Lys Leu Leu Glu Lys Leu Pro NH2

Ala Val Ser Glu His Gln Leu Leu His Asp Lys Gly Lys Ser Ile Gln Asp Leu Arg  (SEQ ID NO:10);

Arg Arg Glu Leu Leu Glu Lys Leu Leu Glu Lys Leu His Thr D-Orn lactam

Ala Val Ser Glu His Gln Leu Leu His Asp Lys Gly Lys Ser Ile Gln Asp Leu Arg  (SEQ ID NO:11); or

Arg Arg Glu Leu Leu Glu Lys Leu Leu Glu Lys Leu His Thr hSer lactam

Ala Val Ser Glu His Gln Leu Leu His Asp Lys Gly Lys Ser Ile Gln Asp Leu Arg  (SEQ ID NO 12).

Arg Arg Glu Leu Leu Glu Lys Leu Leu Glu Lys Leu His Thr HSer Thr His Ile

Gln NH2
```

25. The method of claim 15, wherein the PTHrP analog is administered systemically.

26. The method of claim 25, wherein the PTHrP analog is administered by nasal delivery.

27. The method of claim 15, further comprising locally administering a second bone healing agent to the fracture.

28. The method of claim 15, wherein the fracture is in intramembraneous bone.

* * * * *